United States Patent
Buela et al.

(10) Patent No.: US 11,085,082 B2
(45) Date of Patent: Aug. 10, 2021

(54) METHODS, TOOLS AND SYSTEMS FOR THE PREDICTION AND ASSESSMENT OF GESTATIONAL DIABETES

(71) Applicant: Patia Biopharma, S.A. de C.V., Mexico City (MX)

(72) Inventors: Laureano Simón Buela, Mexico City (MX); Mirella G. Zulueta, Mexico City (MX); Teresa Tusié, Mexico City (MX)

(73) Assignee: Patia Biopharma S.A. de C.V., Ciudad de México (MX)

( * ) Notice: Subject to any disclaimer, the term of this patent is extended or adjusted under 35 U.S.C. 154(b) by 102 days.

(21) Appl. No.: 16/063,081

(22) PCT Filed: Dec. 16, 2016

(86) PCT No.: PCT/EP2016/081427
§ 371 (c)(1),
(2) Date: Jun. 15, 2018

(87) PCT Pub. No.: WO2017/103106
PCT Pub. Date: Jun. 22, 2017

(65) Prior Publication Data
US 2020/0283850 A1    Sep. 10, 2020

(30) Foreign Application Priority Data

Dec. 16, 2015  (GB) .................................... 1522190

(51) Int. Cl.
| | | |
|---|---|---|
| *C12Q 1/68* | (2018.01) | |
| *C07H 21/04* | (2006.01) | |
| *C12Q 1/6883* | (2018.01) | |
| *G16H 50/30* | (2018.01) | |
| *A61K 31/155* | (2006.01) | |
| *A61K 33/20* | (2006.01) | |

(52) U.S. Cl.
CPC .......... *C12Q 1/6883* (2013.01); *A61K 31/155* (2013.01); *A61K 33/20* (2013.01); *G16H 50/30* (2018.01); *C12Q 2531/107* (2013.01); *C12Q 2561/101* (2013.01); *C12Q 2563/159* (2013.01); *C12Q 2565/629* (2013.01); *C12Q 2600/118* (2013.01); *C12Q 2600/156* (2013.01); *G01N 2800/50* (2013.01)

(58) Field of Classification Search
None
See application file for complete search history.

(56) References Cited

U.S. PATENT DOCUMENTS 5,474,796 A * 12/1995 Brennan .............. B01J 19/0046
    422/547

OTHER PUBLICATIONS

Affymetrix, "Axiom® Exome Genotyping Array; dbSNP RS ID (rs7903146)," https://www.affymetrix.com, Dec. 21, 2014; retrieved from the internet on Mar. 2, 2017 (1 page).
Huerta-Chagoya et al., "Genetic Determinants for Gestational Diabetes Mellitus and Related Metabolic Traits in Mexican Women," *PLOS One* 10(5):e0126408, 2015 (17 pages).
Norden-Krichmar et al., "Protective Variant Associated with Alcohol Dependence in a Mexican American Cohort," *BMC Med Genet.* 15:136, 2014 (10 pages).
PCT/EP2016/081427 International Search Report dated Jun. 1, 2017 (5 pages).
PCT/EP2016/081427 Written Opinion dated Jun. 1, 2017 (10 pages).

* cited by examiner

Primary Examiner — Jeanine A Goldberg
(74) Attorney, Agent, or Firm — Klarquist Sparkman, LLP

(57) ABSTRACT

Provided is a method of assessing Gestational Diabetes Mellitus (GDM) susceptibility in a female human subject, the method comprising determining the identity of at least one allele at each of at least two positions of single nucleotide polymorphism (SNP) selected from: TCF7L2—rs7903146; IGF2BP2—rs4402960; CDKN2A/B—rs10811661; SLC16A11—rs13342232; FTO—rs8050136; SLC30A8—rs13266634; CDC123/CAMK1D—rs12779790; KCNQ1—rs2237892; CUBN—rs11254363; CUBN—rs1801222; FIGN—rs2119289; FIGN—rs982393; MTHFR—rs1801131; MTHFR—rs1801133; MTR—rs1805087; and SLC19A1—rs1051266, and/or an SNP in linkage disequilibrium therewith at $r^2 > 0.8$. Also provided are genotyping tools and risk assessment systems for use in the method of assessing GDM susceptibility.

9 Claims, No Drawings
Specification includes a Sequence Listing.

METHODS, TOOLS AND SYSTEMS FOR THE PREDICTION AND ASSESSMENT OF GESTATIONAL DIABETES

CROSS REFERENCE TO RELATED APPLICATIONS

This is the U.S. National Stage of International Application No. PCT/EP2016/081427, filed Dec. 16, 2016, which was published in English under PCT Article 21(2), which in turn claims the benefit of Great Britain Application No. 1522190.6, filed Dec. 16, 2015, which is incorporated herein by reference in its entirety.

SEQUENCE LISTING

The Sequence Listing is submitted as an ASCII text file in the form of the file named 6947-100911-01_ST25.txt, which was created on Dec. 26, 2019, and is ~21 kilobytes, which is incorporated by reference herein.

FIELD OF THE INVENTION

The present invention relates to methods and products, in particular arrays and related systems, for in vitro genotyping of Gestational Diabetes Mellitus (GDM) associated genetic variations and to methods for assessment of gestational diabetes risk among pregnant females.

BACKGROUND TO THE INVENTION

GDM is a condition of carbohydrate intolerance of varying severity that begins or is first recognized during pregnancy and is a common obstetric complication. GDM is characterized by an impaired compensatory increase in insulin secretion to overcome pregnancy-induced insulin resistance. It has been reported that GDM is a strong risk factor for developing Type 2 Diabetes (T2D) in later life, and GDM influences the metabolic health of offspring in the short and long term (Veeraswamy S., et al., *Diabetes Research and Clinical Practice,* 2012, Vol. 97, No. 3, pp. 350-358).

In contrast with T2D, the genetics of GDM have been less studied. Variants within TCF7L2, TNF and HNF4A loci have been associated with the risk of developing GDM in Mexican women (Watanabe R. M., et al. *Diabetes,* 2007, Vol. 56(5), pp. 1481-1485; Guzman-Flores J. M., et al. *Journal of Investigative Medicine,* 2013, Vol. 61(2), pp. 265-269; Reyes-Lopez R., et al. *Diabetes/Metabolism Research and Reviews,* 2014; Monroy V. S., et al., *Journal of Investigative Medicine,* 2014, Vol. 62(3), pp. 632-634). Moreover, a recent reports association between GDM and a TCF7L2 haplotype (CTTC: rs7901695, rs4506565, rs7903146, r512243326) and a KCNQ1 haplotype (TTT: rs2237892, rs163184, rs2237897) (Huerta-Chagoya A., et al., *PLoS ONE,* 2015, Vol. 10(5), pp. 1-17). Interestingly, the authors did not find an association between GDM and a T2D risk haplotype, SLC16A11, that has been reported for Mexican subjects (The SIGMA Consortium: Sequence variants in SLC16A11 are a common risk factor for type 2 diabetes in Mexico. *Nature* (2014) Vol. 506, pp. 97-101).

There remains an unmet need for reliable predictors of GDM susceptibility, particularly for use in ethnically diverse populations such as that of Mexico. The present invention address this and other needs.

SUMMARY OF THE INVENTION

Broadly, the present inventors have found that certain combinations of polymorphisms, particularly single nucleotide polymorphisms (SNPs), are associated with prediction of Gestational Diabetes Mellitus (GDM) risk. Further, combinations of SNPs selected for particular suitability to Mexican and Latin American populations, among others, have been identified herein. Tools and associated systems have been developed for use in methods of the invention, including for the prediction of GDM susceptibility among pregnant women.

Accordingly, in a first aspect the present invention provides a method of assessing Gestational Diabetes Mellitus (GDM) susceptibility in a female human subject, the method comprising determining the identity of at least one allele at each of at least 2, 3, 4, 5, 6, 7, 8, 9, 10, 11, 12, 13, 14, 15 or 16 positions of single nucleotide polymorphism (SNP) selected from:

TCF7L2—rs7903146;
IGF2BP2—rs4402960;
CDKN2A/B—rs10811661;
SLC16A11—rs13342232;
FTO—rs8050136;
SLC30A8—rs13266634;
CDC123/CAMK1D—rs12779790;
KCNQ1—rs2237892;
CUBN—rs11254363;
CUBN—rs1801222;
FIGN—rs2119289;
FIGN—rs982393;
MTHFR—rs1801131;
MTHFR—rs1801133;
MTR—rs1805087; and
SLC19A1—rs1051266, and/or an SNP in linkage disequilibrium therewith at $r^2>0.8$, $r^2>0.9$, $r^2>0.95$, $r^2>0.99$ or $r^2=1.0$.

The SNPs may be as disclosed in the NCBI dbSNP, *Homo sapiens* genome build 37.

In some cases in accordance with the first aspect of the invention, the method comprises determining the identity of at least one allele at each of the following SNPs:

TCF7L2—rs7903146; and
KCNQ1—rs2237892.

In some cases in accordance with the first aspect of the invention, the method comprises determining the identity of at least one allele at each of the following SNPs:

TCF7L2—rs7903146;
IGF2BP2—rs4402960;
CDKN2A/B—rs10811661;
SLC16A11—rs13342232;
FTO—rs8050136;
SLC30A8—rs13266634;
CDC123/CAMK1D—rs12779790;
KCNQ1—rs2237892;
CUBN—rs11254363;
CUBN—rs1801222;
FIGN—rs2119289;
FIGN—rs982393;
MTHFR—rs1801131;
MTHFR—rs1801133;
MTR—rs1805087; and
SLC19A1—rs1051266.

In some cases in accordance with the first aspect of the invention, allele determination is carried out at not more than 50, 40, 30, 25, 20, 19, 18, 17 or not more than 16 SNP positions.

In some cases in accordance with the first aspect of the invention presence of one or more of the following risk alleles (i.e. heterozygous or homozygous risk allele) indicates that the subject has greater susceptibility to GDM:

T at rs7903146;
T at rs4402960;
T at rs10811661;
G at rs13342232;
A at rs8050136;
C at rs13266634;
G at rs12779790;
T at rs2237892;
G at rs11254363;
T at rs1801222;
G at rs2119289;
A at rs982393;
C at rs1801131;
A at rs1801133;
G at rs1805087; and
A at rs1051266.

In some cases in accordance with the first aspect of the invention the method comprises determining the identity of both alleles at each SNP thereby obtaining the genotype of the subject at each SNP.

In some cases in accordance with the first aspect of the invention the subject is determined to be heterozygous or to be homozygous for the risk allele at at least one of said SNPs. In the case where the subject is found to have one or more risk alleles the subject may be classified as being at greater risk of GDM in comparison with a subject having none of said risk alleles or having fewer of said risk alleles.

In some cases in accordance with the first aspect of the invention the method comprises assaying a DNA-containing sample that has previously been obtained from said subject. In particular, the sample may be selected from the group consisting of: blood, hair, skin, amniotic fluid, buccal swab, saliva, and faeces. A particularly preferred sample is whole blood, from which has been isolated genomic DNA.

In some cases in accordance with the first aspect of the invention the method comprises isolating and/or amplifying genomic DNA from said subject.

In some cases in accordance with the first aspect of the invention determining the identity of said at least one allele at each SNP comprises: probe hybridization, real time PCR, array analysis, bead analysis, primer extension, restriction analysis and/or DNA sequencing.

In some cases the method employs a plurality of oligonucleotide probes, which plurality includes a pair of allele-specific oligonucleotide probes for each SNP, said allele-specific oligonucleotide probes each spanning the polymorphic position as set forth in the context sequence column of Table 2. Generally such oligonucleotides will be of length 10-50 nucleotides, preferably 12-20 nucleotides, and more preferably 13-18 nucleotides. The skilled person is readily able to design probes that span the SNPs, e.g. making use of the sequence context shown in Table 2. Typically an oligonucleotide probe will comprise of consist of a contiguous sequence of the above-mentioned lengths of the sequence context shown in Table 2 with the polymorphic position typically being located at a central position in each of the allele-specific probes, or its reverse complement or which hybridizes thereto (e.g. under conditions of high stringency).

In some cases determining the identity of said at least one allele at each SNP comprises TaqMan® SNP genotyping. In particular, the method may employ TaqMan® OpenArray® SNP genotyping.

In some cases determining the identity of said at least one allele at each SNP comprises the use of a platform based in an integrated fluidic circuits (IFCs) system, for genotyping. Such platforms are available from, e.g., Fluidigm. In certain cases the platform is a Dynamic Array IFC Genotyping Platform.

In some cases in accordance with the first aspect of the invention the method comprises determining the number of and identity of SNP risk alleles, and wherein the method further comprises computing a GDM risk score for said subject.

In some cases the method comprises inputting the SNP risk allele determinations into a probability function to compute said risk score.

In some cases in accordance with the first aspect of the invention the subject is a female of reproductive age. In particular, the subject may be pregnant (e.g. may have tested positive in a pregnancy test). In some cases, the subject may be of <20 gestational week.

In some cases in accordance with the first aspect of the invention the subject is of Mexican or Latino American origin or ancestry. In some cases the subject is of African-American, Afro-Caribbean, South Asian, Polynesian, Native American or Hispanic origin.

In some cases in accordance with the first aspect of the invention the subject has at least one first degree relative who has, or has previously been diagnosed with, GDM and/or T2D.

In some cases in accordance with the first aspect of the invention the subject has one or more clinical risk factors for GDM selected from: pregestational body mass index (BMI) >30; waist circumference>80 cm; age>35; diagnosis of polycystic ovary syndrome; a previous diagnosis of GDM (e.g. during a previous pregnancy); is a smoker; a previous pregnancy that resulted in a child with high birth weight (e.g. >$90^{th}$ centile); and a previous diagnosis of prediabetes, impaired glucose tolerance or impaired fasting glycaemia.

In some cases in accordance with the first aspect of the invention the subject is determined to carry one or more of said risk alleles at one or more (e.g. 1, 2, 3, 4, 5, 6, 7, 8, 9, 10, 11, 12, 13, 14, 15 or 16) of said SNPs and therefore to be at greater risk of GDM, the method further comprising administering to the subject a test selected from the group consisting of: an oral glucose tolerance test (OGTT); a non-challenge blood glucose test; a screening glucose challenge test; and a urinary glucose test. In particular, the test may be used to diagnose or confirm GDM in a subject identified as being at risk of developing GDM on the basis of the presence of one or more of said risk alleles.

In some cases in accordance with the first aspect of the invention the subject is determined to carry one or more of said risk alleles at one or more (e.g. 1, 2, 3, 4, 5, 6, 7, 8, 9, 10, 11, 12, 13, 14, 15 or 16) of said SNPs and therefore to be at greater risk of GDM, the method further comprising an intervention selected from the group consisting of: a low glycemic index (GI) diet, increased exercise, insulin therapy, and anti-diabetic medication (e.g. metformin or glyburide).

In a second aspect the present invention provides a genotyping tool for use in a method of the first aspect of the invention, said tool comprising an array having a plurality of oligonucleotide probe pairs, each of said probe pairs comprising a first probe specific for a first allele of a single nucleotide polymorphism (SNP) and a second probe specific for a second allele of the SNP, wherein said plurality of oligonucleotide probe pairs comprises probe pairs that interrogate at least two SNPs selected from the group consisting of:
TCF7L2—rs7903146;
IGF2BP2—rs4402960;
CDKN2A/B—rs10811661;

SLC16A11—rs13342232;
FTO—rs8050136;
SLC30A8—rs13266634;
CDC123/CAMK1D—rs12779790;
KCNQ1—rs2237892;
CUBN—rs11254363;
CUBN—rs1801222;
FIGN—rs2119289;
FIGN—rs982393;
MTHFR—rs1801131;
MTHFR—rs1801133;
MTR—rs1805087; and
SLC19A1—rs1051266,
and/or an SNP in linkage disequilibrium with any one of said SNPs at $r^2>0.8$, $r^2>0.9$, $r^2>0.95$, $r^2>0.99$ or $r^2=1.0$.

In some cases the oligonucleotide probes of the array that interrogate SNPs selected from: rs7903146; rs4402960; rs10811661; rs13342232; rs8050136; rs13266634; rs12779790; rs2237892; rs11254363; rs1801222; rs2119289; rs982393; rs1801131; rs1801133; rs1805087; and rs1051266, make up at least 50%, at least 60%, at least 70%, at least 80%, at least 90%, at least 95%, at least 99% of the total number of nucleic acid probes in the array, or essentially all of the nucleic acid probes in the array. In this way the genotyping tool is enriched for probes that interrogate SNPs informative for GDM risk prediction. By avoiding a high proportion of probes that interrogate other SNPs (e.g. as is typically seen in large-scale SNP microarrays), the genotyping tool of the present invention may provide a more efficient tool for assessment of GDM risk prediction whereby use of unnecessary probes and other reagents is minimized.

In some cases said plurality of oligonucleotide probe pairs comprises probe pairs that interrogate at least:
TCF7L2—rs7903146; and
KCNQ1—rs2237892.

In some cases said plurality of oligonucleotide probe pairs comprises probe pairs that interrogate at least:
TCF7L2—rs7903146;
IGF2BP2—rs4402960;
CDKN2A/B—rs10811661;
SLC16A11—rs13342232;
FTO—rs8050136;
SLC30A8—rs13266634;
CDC123/CAMK1D—rs12779790;
KCNQ1—rs2237892;
CUBN—rs11254363;
CUBN—rs1801222;
FIGN—rs2119289;
FIGN—rs982393;
MTHFR—rs1801131;
MTHFR—rs1801133;
MTR—rs1805087; and
SLC19A1—rs1051266.

In some cases the total number of different SNPs for which allele-specific probes are provided does not exceed 50, 40, 30, 25, 20, 19, 18, 17 or 16.

In some cases the allele-specific oligonucleotide probes are each covalently attached to a fluorophore, to a quencher and/or to a minor groove binding domain (MGB). Preferably, each member of an allele-specific probe pair is conjugated to a different fluorophore enabling specific detection of the probe pair members by fluorescence wavelength.

In some cases the nucleotide sequence of each of the allele-specific probes is:
(i) a contiguous nucleotide sequence of 10-25, preferably 13-18 nucleotides, of the sequence context set forth for each SNP in Table 2, wherein the probe sequence spans the polymorphic position; or
(ii) the complement of (i).

In some cases the genotyping tool further comprises a primer pair for each of said SNPs, said primer pair for each SNP comprising an oligonucleotide primer that hybridizes to a target sequence upstream of the SNP and an oligonucleotide primer that hybridizes to a target sequence downstream of the SNP.

In some cases the tool further comprises one or more reagents for amplification of DNA comprising said SNPs and/or for detection of said allele-specific probes. In particular, the tool reagents may include Taq DNA polymerase.

In some cases the array comprises an OpenArray® of between 1000 and 10000 array positions. For example, the array may comprise 3072 through-holes, each acting as a nanoliter-scale reactor (e.g. 33 nL).

Preferably, the tool is in the form of a TaqMan® OpenArray® SNP genotyping platform or an integrated fluidic circuits (IFC) genotyping platform.

In a third aspect, the present invention provides a Gestational Diabetes Mellitus (GDM) risk assessment system for use in a method of the first aspect of the invention, the system comprising a genotyping tool of the second aspect of the invention and a computer programmed to compute a GDM risk score from the genotype data of the subject at each of said at least two SNPs.

In some cases the computer computes the risk score from the genotype data by applying a weighting or coefficient to each SNP risk allele found to be present such that the contribution of to the risk score is proportional to that SNP's contribution to GDM risk, e.g. a weighting commensurate with an odds ratio for the association of the SNP to GDM.

In accordance with the first aspect of the present invention the method of the invention may employ a genotyping tool of the second aspect of the invention or a GDM risk assessment system of the third aspect of the invention.

The present invention includes the combination of the aspects and preferred features described except where such a combination is clearly impermissible or is stated to be expressly avoided. These and further aspects and embodiments of the invention are described in further detail below and with reference to the accompanying example.

DETAILED DESCRIPTION

Single Nucleotide Polymorphisms (SNPs)

SNPs are identified herein using the rs identifier numbers in accordance with the NCBI dbSNP database, which is publically available at: http://www.ncbi.nlm.nih.gov/projects/SNP/. As used herein, rs numbers refer to the dbSNP *Homo sapiens* build 37.1 available from 2 Feb. 2010.

Linkage Disequilibrium (LD)

In some embodiments, SNPs in linkage disequilibrium with the SNPs associated with the invention are useful for obtaining similar results. As used herein, linkage disequilibrium refers to the non-random association of SNPs at two or more loci. Techniques for the measurement of linkage disequilibrium are known in the art. As two SNPs are in linkage disequilibrium if they are inherited together, the information they provide is correlated to a certain extent. SNPs in linkage disequilibrium with the SNPs included in the models can be obtained from databases such as HapMap or other related databases, from experimental setups run in laboratories or from computer-aided in silico experiments. Determining the genotype of a subject at a position of SNP as specified herein, e.g. as specified by NCBI dbSNP rs identifier, may comprise directly genotyping, e.g. by determining the identity of the nucleotide of each allele at the locus of SNP, and/or indirectly genotyping, e.g. by determining the identity of each allele at one or more loci that are in linkage disequilibrium with the SNP in question and which allow one to infer the identity of each allele at the locus of SNP in question with a substantial degree of confidence. In some cases, indirect genotyping may comprise determining the identity of each allele at one or more loci that are in sufficiently high linkage disequilibrium with the SNP in question so as to allow one to infer the identity of each allele at the locus of SNP in question with a probability of at least 90%, at least 95% or at least 99% certainty.

As will be appreciated by the reader, in some cases one or more polymorphisms or alterations in linkage disequilibrium with a polymorphism or alteration disclosed herein may find use the methods of the present invention. Linkage disequilibrium (LD) is a phenomenon in genetics whereby two or more mutations or polymorphisms are in such close genetic proximity that they are co-inherited. This means that in genotyping, detection of one polymorphism as present infers the presence of the other. Thus, a polymorphism or alteration in such linkage disequilibrium acts as a surrogate marker for a polymorphism or alteration as disclosed herein. Preferably, reference herein to a polymorphism or alteration in linkage disequilibrium with another means that $r^2>0.8$, preferably $r^2>0.9$, more preferably $r^2>0.95$ or even $r^2>0.99$. In particularly preferred embodiments, an SNP is considered to be in LD with an SNP set forth in Table 1 if it exhibits $r^2=1.0$ and $D'=1.0$.

As used herein, LD is preferably determined in a Mexican or Latino American population.

In one example, the SNPs rs7903146, rs7901695, rs4506565 and rs12243326 form an LD block, such that rs7901695, rs4506565 and/or rs12243326 may in some cases be used, in accordance with any aspect of the present invention, as a proxy SNP for rs7903146. In particular, rs7901695-rs4506565-rs7903146-rs12243326 constitutes a GDM risk haplotype C-T-T-C. Thus, presence of the risk allele T at rs7903146 may be inferred from a determination that the subject has C at rs7901695, T at rs4506565 and/or C at rs12243326.

In another example, the SNPs rs2237892, rs163184 and rs2237897 form an LD block, such that rs163184 and/or rs2237897 may in some cases be used, in accordance with any aspect of the present invention, as a proxy SNP for rs2237892. In particular, rs2237892-rs163184-rs2237897 constitutes a GDM risk haplotype T-T-T. Thus, presence of the risk allele T at rs2237892 may be inferred from a determination that the subject has T at rs163184 and/or T at rs2237897.

Genotyping Assays

Aspects of the invention relate to determining the presence of SNPs through obtaining a patient DNA sample and evaluating the patient sample for the presence of two or more SNPs. It should be appreciated that a patient DNA sample can be extracted, and a SNP can be detected in the sample, through any means known to one of ordinary skill in art. Some non-limiting examples of known techniques include detection via restriction fragment length polymorphism (RFLP) analysis, planar microarrays, bead arrays, sequencing, single strand conformation polymorphism analysis (SSCP), chemical cleavage of mismatch (CCM) and denaturing high performance liquid chromatography (DHPLC).

In some embodiments, a SNP is detected through PCR amplification and sequencing of the DNA region comprising the SNP. In some embodiments SNPs are detected using microarrays. Microarrays for detection of genetic polymorphisms, changes or mutations (in general, genetic variations) such as a SNP in a DNA sequence, comprise a solid surface, typically glass, on which a high number of genetic sequences are deposited (the probes), complementary to the genetic variations to be studied. Using standard robotic printers to apply probes to the array a high density of individual probe features can be obtained, for example probe densities of 600 features per $cm^2$ or more can be typically achieved. The positioning of probes on an array is precisely controlled by the printing device (robot, inkjet printer, photolithographic mask etc) and probes are aligned in a grid. The organisation of probes on the array facilitates the subsequent identification of specific probe-target interactions. Additionally it is common, but not necessary, to divide the array features into smaller sectors, also grid-shaped, that are subsequently referred to as sub-arrays. Sub-arrays typically comprise 32 individual probe features although lower (e.g. 16) or higher (e.g. 64 or more) features can comprise each subarray.

In some embodiments, detection of genetic variation such as the presence of a SNP involves hybridization to sequences which specifically recognize the normal and the risk allele in a fragment of DNA derived from a test sample. Typically, the fragment has been amplified, e.g. by using the polymerase chain reaction (PCR), and labelled e.g. with a fluorescent molecule. A laser can be used to detect bound labelled fragments on the chip and thus an individual who is homozygous for the normal allele can be specifically distinguished from heterozygous individuals (in the case of autosomal dominant conditions then these individuals are referred to as carriers) or those who are homozygous for the risk allele. In some embodiments, the amplification reaction and/or extension reaction is carried out on the microarray or bead itself.

In some embodiments, methods described herein may involve hybridization. For differential hybridization based methods there are a number of methods for analysing hybridization data for genotyping:

Increase in hybridization level: The hybridization levels of probes complementary to the normal and mutant alleles are compared.

Decrease in hybridization level: Differences in the sequence between a control sample and a test sample can be identified by a decrease in the hybridization level of the totally complementary oligonucleotides with a reference sequence. A loss approximating 100% is produced in mutant homozygous individuals while there is only an approximately 50% loss in heterozygotes. In Microarrays for examining all the bases of a sequence of "n" nucleotides ("oligonucleotide") of length in both strands, a minimum of "2n" oligonucleotides that overlap with the previous oligonucleotide in all the sequence except in the nucleotide are necessary. Typically the size of the oligonucleotides is about 25 nucleotides. However it should be appreciated that the oligonucleotide can be any length that is appropriate as would be understood by one of ordinary skill in the art. In particular, the use of a minor groove binding domain (MBD) permits shorter probe sequences while retaining high discrimination between the perfect match and the mismatch. The increased number of oligonucleotides used to reconstruct the sequence reduces errors derived from fluctuation of the hybridization level. However, the exact change in sequence cannot be identified with this method; in some embodiments this method is combined with sequencing to identify the mutation.

Where amplification or extension is carried out on the microarray or bead itself, three methods are presented by way of example:

In the Minisequencing strategy, a mutation specific primer is fixed on the slide and after an extension reaction with fluorescent dideoxynucleotides, the image of the Microarray is captured with a scanner.

In the Primer extension strategy, two oligonucleotides are designed for detection of the wild type and mutant sequences respectively. The extension reaction is subsequently carried out with one fluorescently labelled nucleotide and the remaining nucleotides unlabelled. In either case the starting material can be either an RNA sample or a DNA product amplified by PCR.

In the Tag arrays strategy, an extension reaction is carried out in solution with specific primers, which carry a determined 5' sequence or "tag". The use of Microarrays with oligonucleotides complementary to these sequences or "tags" allows the capture of the resultant products of the extension. Examples of this include the high density Microarray "Flex-flex" (Affymetrix).

For cost-effective genetic diagnosis, in some embodiments, the need for amplification and purification reactions presents disadvantages for the on-chip or on-bead extension/amplification methods compared to the differential hybridization based methods. However the techniques may still be used to detect and diagnose conditions according to the invention.

Typically, Microarray or bead analysis is carried out using differential hybridization techniques. However, differential hybridization does not produce as high specificity or sensitivity as methods associated with amplification on glass slides. For this reason the development of mathematical algorithms, which increase specificity and sensitivity of the hybridization methodology, are needed (Cutler D J, Zwick M E, Carrasquillo M N, Yohn C T, Tobi K P, Kashuk C, Mathews D J, Shah N, Eichler E E, Warrington J A, Chakravarti A. Genome Research; 11:1913-1925 (2001). Methods of genotyping using microarrays and beads are known in the art.

The genotyping platform for use in the methods of the present invention may be based on the TaqMan® OpenArray® SNP Genotyping system available from Life Technologies. Further details of the TaqMan® genotyping system and OpenArray® format are available from the Life Technologies, Applied Biosystems, webpage, e.g., the TaqMan® OpenArray® Genotyping Getting Started Guide, © 2010 Life Technologies Corporation.

Alternatively or additionally, the genotyping platform for use in the methods of the present invention may be based on the Dynamic Array IFCs Genotyping System from Fluidigm. Further details of the Dynamic Array IFCs Genotyping System are available from Fluidigm webpage.

EXAMPLE

Example 1—Selection of 16 Single Nucleotide Polymorphisms (SNPs) for a GDM Genetic Prediction Tool in Mexican (and Latino) Populations A consensus list of SNPs was generated (Table 1). Our initial study included a total 243 SNPs to test for possible association to GDM based on the following criteria:

a) Previously associated to GDM or other adverse traits related to pregnancy (i.e. macrosomy) in different populations.

b) Previously associated to T2D in different populations. As GDM increases the mother's (and offspring's) risk to develop T2D, it is expected that some of the gene variants increase the risk of both T2D and GDM.

c) Previously identified through GWAS analyses and having a significant p value for these kind of studies.

d) Previously replicated for association in two different populations.

From the total of SNP analyzed the ones selected for the array (16) showed significant association for GDM, pregnancy related traits or T2D in Mexican women.

Table 2 shows target genes, SNP rs identifiers, chromosome and nucleotide location (build 37) and SNP context sequence for each of the 16 SNPs.

The present inventors recently found an association between GDM and a TCF7L2 haplotype (CTTC: rs7901695, rs4506565, rs7903146, r512243326) and a KCNQ1 haplotype (TTT: rs2237892, rs163184, rs2237897) (Huerta-Chagoya A., et al., *PLoS ONE*, 2015, Vol. 10(5), pp. 1-17, e0126408, doi:10.1371/journal.pone.0126408, the entire contents of which are expressly incorporated herein by reference).

TABLE 1

SNPs of DIABETESpregest Tool

| No. | SNP | Chr. | Locus (bp) | Gene | Risk allele | Allele frequency | Odds Ratio | P Value |
|---|---|---|---|---|---|---|---|---|
| 1 | rs7903146 | 10 | 114758349 | TCF7L2 | T | 0.30 | 2.07 (1.44-2.98) | 0.00324 |
| 2 | rs4402960 | 3 | 185511687 | IGF2BP2 | T | 0.33 | 1.12 (1.04-1.20) | |
| 3 | rs10811661 | 9 | 143490235 | CDKN2A/B | T | 0.85 | 1.17 (1.08-1.27) | |
| 4 | rs13342232 | 17 | 6945940 | SLC16A11 | G | 0.30 | 1.29 (1.20-1.38) | $5.5 \times 10^{-12}$ |
| 5 | rs8050136 | 16 | 53816275 | FTO | A | 0.41 | 1.17 (1.08-1.27) | $1.1 \times 10^{-4}$ |
| 6 | rs13266634 | 8 | 118184783 | SLC30A8 | C | 0.70 | 1.12 (1.05-1.21) | $1.8 \times 10^{-3}$ |
| 7 | rs12779790 | 10 | 12328010 | CDC123/CAMK1D | G | 0.20 | 1.16 (1.08-1.24) | $2.3 \times 10^{-5}$ |
| 8 | rs2237892 | 11 | 2839751 | KCNQ1 | T | 0.48 | | |
| 9 | rs11254363 | 10 | 17130693 | CUBN | G | 0.28 | | |
| 10 | rs1801222 | 10 | 17156151 | CUBN | T | 0.16 | | |
| 11 | rs2119289 | 2 | 164497946 | FIGN | G | 0.12 | | |

TABLE 1-continued

SNPs of DIABETESpregest Tool

| No. | SNP | Chr. | Locus (bp) | Gene | Risk allele | Allele frequency | Odds Ratio | P Value |
|---|---|---|---|---|---|---|---|---|
| 12 | rs982393 | 2 | 164490529 | FIGN | A | 0.12 | | |
| 13 | rs1801131 | 1 | 11854476 | MTHFR | C | 0.12 | | |
| 14 | rs1801133 | 1 | 11856378 | MTHFR | A | 0.56 | | |
| 15 | rs1805087 | 1 | 237048500 | MTR | G | 0.20 | | |
| 16 | rs1051266 | 21 | 46957794 | SLC19A1 | A | 0.40 | | |

TABLE 2

SNP Context Sequence

| Target Gene | rsID | Context sequence | SNP |
|---|---|---|---|
| TCF7L2 | rs7903146 | GCACATGTGAAAGAAAAAGGGAGAAAGCAGGATTGAGCAGGGGGAGCCGTCAGATGGTAATGCAG ATGTGATGAGATCTCTGCCGGACCAAAGAGAAGATTCCTTTTTAAATGGTGACAAATTCATGGGC TTTCTCTGCCTCAAAACCTAGCACAGCTGTTATTTACTGAACAATTAGAGAGCTAAGCACTTTTT AGATA[C/T]TATATAATTTAATTGCCGTATGAGGCACCCTTAGTTTTCAGACGAGAAACCACAG TTACAGGGAAGGCAAGTAACTTAGTCAATGTCAGATAACTAGGAAAAGGTTAGAGGGGCCCTGGA CACAGGCCTGTGTGACTGAGAAGCTTGGGCACTTCACTGCTACATTTCATCTCTTCGCTATAAAC ATTTTAGCTTTTTGT (SEQ ID NO: 1) | [C/T] |
| IGF2BP2 | rs4402960 | GCTGGAGTTGGTTTCTGGCCTCCTCCAGGCTCCCCTGCATCAAGCGCAGCTGAGCAGTTCCCTGT AATGGGGAGAGGGTCTGTCCCTTTATCTGGAGCCTCCAGTTTTGAAAATCAGCCCTGGATCTCCA ACTGCTGCCCAGTCTGGCTGTTCAGCAGGCCCCATGCCCCCCTTTCCCCAGTCTTGAGGCCTGGG ACTAGGGCTGTCAGGCACGTCTGCCACGTCTGCCCCTCTCTCCCCTGCGGCCAGCCCTCTACAGC CACAAGCCC[G/A]AGGTGGCCCAGTACACCCACACGGGCCTGCTCCCGCAGACTATGCTCATCA CCGACACCACCAACCTGAGCGCCCTGGCCAGCCTCACGCCCACCAAGCAGGTAAGGTCCAGGCCT GCTGGCCCTCCCTTGGCCTGTGACAGAGCCCCTCACCCCCACATCCCCCGGGCTCAGGAGGCTGC TCTGCTCCCCAGGTCTTCACCTCAGACACTGAGGCCTCCAGTGAGTCGGGCTTCACACGCCGG CATCTCAGGCCACCACCCTCCACGTCCCCAGCCA (SEQ ID NO: 2) | [G/T] |
| CDKN2A/B | rs10811661 | ATATTGACAAAGTTTCAGTTAAGCAGATGAAATTCTAAGAGTTAAGCTGGGATTTTCCAAAATAA TTCCTGTTAACAGACTGAAAGCACTTATCAGTTCTGTCTAATGAAGACATTAGAACACCATAACC TTTCCGGCCCATTTTCTTTGTCAATAAGCGTTCTTGCCCTGTCAGCAGCTCACCTCCAGCTTTAG TTTTC[C/T]CATGACAGTAAGTCTATTACCCTCCTGATCTGTCTTCTGGCTCCTCCTACCCAGG ATGGGGAAGGTTTTTGACTTTACTGATATTCTCAGAACAAATTTTGGGAAGTAAATATAAGGTTT TCCAGTCGGGTGCAGTGGCTCACGCCTATGATCCCAGCGCTTTGGGAAACCAAGGTGGGTGGATC ACCTGAGGTCAGGAG (SEQ ID NO: 3) | [C/T] |
| SLC16A11 | rs13342232 | CTAAAGCGTGGGGAGCCAAGTGCACGTAAGGAACGAAGTACCCGCCCCCAACCAGGGCTGTGCCT AGAGCAAAGATTGAGAAGGCCCGGCGTGTGAACAGACTCAGGCCGAGGGCAGCTAGGGGACTACG CGGTGGGGCTGGGGGGTCTCCAGGAAGGACCAGGGGTAGCAGCAGGGCGCCACAGGGGGTGAGGT GGAGGGTGATCGCGCCGAGGAGGAGCAGGAGCGCCCCGCCAGCCGAAAGTATCGAG[A/G]AGAAG CTGCAAGGCGGGCGCCAGGAGCAGCGAGGAGGCCCCGTTGCCGGTGAGCGCCAGCCCCACCGCCA AGACTCGACGGCGGGAGAAGTAACGCGAGAGGGTGCCTAGGGCGGGGGCGAACACCAGGGCCCAA CCAAAGCCTGCGAATGAATAGGAGGGGATGGGGGCCGGCACTGGGGACGCCCGCCCCAGCATTCC CAGCCCGGCTCTCCGCACCAGGCCCCCGCCTCGTTCGCTACCCCAGATCC (SEQ ID NO: 4) | [A/G] |
| FTO | rs8050136 | CTGGCACATCAGGGTTCAGATTTCTGCTGTGCTACTTCTTGGCTGTGTTTTGGCACGTGAACTTC TCTACACCTCAGTTTCTTTGTTTATGTAATGGGGATTCATATGACAATTAAAGAGAGAGCTTGTC TAAAGTGTCTTATGTAGTAGTATCCCCAGTTTGACCCTTTTGAGAATCTGATGACAGTTATGGAA CCCTCTCCCCAGACAAGTGCCCGTATACCCAGAACTTTGTATTTAATTTCATGGGGTTCATGAAG CCTCTGAAACTCAGCTTAAGAGTCCATACCAACCAAGGTCCTTATAGGAAGAGCTTGTGTTTTTG TTTTGTTTTGGCTTTCTGCAGTCTCTTAATAATGTTTATTGAATGAGAGAATTTAACTAATTTCC GGTTTCCATAATCACTTTAAACTCGGTATTTGATTTCCTTTTCCCTGGGACCTGTGACAGTGCCA GCTTCATAGCCTAGTCTAGGCACCCACTGTGGCAAT[A/C]AATATCTGAGCCTGT GGTTTTTGCCTTAGGTAAACTGTAGAGATGGACTCATGGAATGCTTGGAAAATTTTTCAGTTTAT GATAATGTGTAAATGTCGAGAGCCAATTATTGAGGAATGGCACCTCAAAGTATTTGGGTACTCTA GATCAGACATGACCATCTTGGTGTGTGAAATTTTGCTAATGCATCTTTCCTAATAGAATATACAA TCTCAGGGCTAGAAAGTCTTAGAGATCATTTAATTTAATTCCTCCAGATTGATTAAGTGGTTTGT CCAAGGTCATTCAACTGGTATAGTGGCAGAGCTCAGGCTGTACAAATCAGGTGAGTATTCTTCAG CTCCTCAGAAGCCAGTAACTTCCACTCACTTGTGTGTGTCTGAAATTCATTAAACCTTCGACACA AAGTGCAGCCATTTTAATGCTGAATGATATTCATCACTGTCTGAAATGGGCTTATTTATGTACGA ATGTTTATTCCTATCTCTTCCTCCATTCTC (SEQ ID NO: 5) | [A/C] |
| SLC30A8 | rs13266634 | CTGCTGATAGCATTTGGGACAGGAAAAAAATGGCAGTGAGGGTTGCTGCTCTAAGAAAGGTCTGT GGGGAGCTCTAAACGCTTCCTGGTTCCTGTCACTATCCTTGATATAAATTCTGATTACATACAAA GCCTGCAACCCAGAGATCCCTGGGAGCTGGTGAGCAGGGCTGTATAAGAAATAATAGTTCTGTCT TGGCTTTTTCCAGGGCTTGTCTCCCCTTCCATAGTAAGCTCCTAGGAATGCCAGACTCCAGAGAT AACAGTGGACAGAAAGAGTTCCCATAGCGACAGGGCACTTTGCTGCACTAGAGTTTCCCCTGCCT TGTCTGTGTGAATGTAGCTGATTATCAGAGCAAACGTGGCTTCCTCTGAGTGCCCTGCCTCTGCC CCACCCCAGCAGGTCAAAGACAAAGTACTTGAAGTTGGAGTCAGAGCAGTCGCCCATGCGTGTGC AATCAGTGCTAATCTCCCTGTGCTCTTTATCAACAGCAGCCAGC[C/T]GGGACAGCCAAGTGG | [C/T] |

TABLE 2-continued

SNP Context Sequence

| Target Gene | rsID | Context sequence | SNP |
|---|---|---|---|
| | | TTCGGAGAGAAATTGCTAAAGCCCTTAGCAAAAGCTTTACGATGCACTCACTCACCATTCAGATG<br>GAATCTCCAGTTGACCAGGACCCCGACTGCCTTTTCTGTGAAGACCCCTGTGACTAGCTCAGTCA<br>CACCGTCAGTTTCCCAAATTTGACAGGCCACCTTCAAACATGCTGCTATGCAGTTTCTGCATCAT<br>AGAAAATAAGGAACCAAAGGAAGAAATTCATGTCATGGTGCAATGCACATTTTATCTATTTATTT<br>AGTTCCATTCACCATGAAGGAAGAGGCACTGAGATCCATCAATCAATTGGATTATATACTGATCA<br>GTAGCTGTGTTCAATTGCAGGAATGTGTATATAGATTATTCCTGAGTGGAGCCGAAGTAACAGCT<br>GTTTGTAACTATCGGCAATACCAAATTCATCTCCCTTCCAATAATGCATCTTGAGAACACATAGG<br>TAAATTTGAACTCAGGAAAGTCTTACTAGA (SEQ ID NO: 6) | |
| CDC123/<br>CAMK1D | rs12779790 | agattttgggctgaggcgatgggggttttctagatatataatcatgtcatctgcaaacagggacaa<br>cttgactttctcttttcctaattgaatacccttttattcttctcctgcctgattgccctggcca<br>gaacttccaacactacgttgactaggggtggtgagaTACttcttttttttcttttttttgagat<br>ggagtctcgctctgtcgcccaggctggagtgcagtggcgtgatcttggctcactgcaagctccac<br>ctccggggttcacaacattctcctgcctgagcctccgagtaggtgggactgcaggcacccgcca<br>ccacgcgcagctaattttttgtattttagtagagatggggtttcactgtgttagccaggatgg<br>tctcgatctcctgacctcgtgatccgcctgcctcccaaagtctcccaaagtgctgggat<br>tacaggtgtgagccaccgcacccggACAatgttgggaattttttc[A/G]tatttcttggccatt<br>tatatatcttcttttgagaattatctattcatgtccttagcccattttttgatgggatttttttt<br>tcttgctagtttgtttgtgttcattgtagattctggatattagtcctttgtcagatgtatactat<br>ttgtaTCttttttttttggacagagtctcactctgtgcccaggctggagtgcagtggtgtgatc<br>ttggctcactgcaacctccgcctcctgggttcaagcaattctcctacctcagcctcctgagtagc<br>tgggactacaggtgcataccaccacacctggctaattttctgtattttttttttttttttgata<br>gagacggggtttcaccatgttagccaggtgggcttgatctcctgacctcgtgatccacccacct<br>cggcctcccaaagtgctgggattacaggcgtgagccactgcactcagccCTcttttttattatta<br>aaattttttttGGCTAGGCATGGTGGCTCA (SEQ ID NO: 7) | [A/G] |
| KCNQ1 | rs2237892 | AATATGCATTAACACCTAAAACCCACTATCCTGGCAAAAAGTGGCAGGATTGTCTGAAAAACAC<br>ATGGCCAGCCACCCTGCACCCTGAGTTCCACAACATCTAAACCCAGTGTCTGCTGGCCCTCAGAG<br>TGGGAGCGCGTGCCCCAACTTCCGAGCCCTAGGAAAGGGTCTTGTCTGCTCTTCCCCTCAGTGTC<br>AGGTGACCCAAGAGTGTGGGGGTCAGGCAATGGCGTCCTTGTGCCCTTGTCACCCACTCCTGTGGG<br>TACACAGCTTCCCTTTCTGCAAAGTCACACCCCAAGCCCTGGCTTGAGCATGTACACAGGCTGCA<br>GCCCGTGCTGTTCCTGGAGCCACCGTCCCAGGTGTGGCTAAGGCCCCACAGAGTGTGCATCCTAAGG<br>TGGTTCAGAGGTCCTCAGAAAGTGCCAAGAGGCCTTCCTCAGAGGAAGAGCAAGGGTAGGTGCCT<br>CTGGCATGAGCCAGATGATGGGAGCTGTCACAGGACTTTGCCACC[C/T]GGGGTGAGGGGCCTA<br>GAAACCCCTCTCCACCAGATGCCTTACACCCCCATCCCCACACGCACACAGCTTGGAGGCTGGA<br>AGCCCCCGGAATGCGGCCCACCCTGTCTCCAGTTGTTCCCTACCAGCCCAGCTGCTGGTCCCTAA<br>CCGGGCCCACCTGTTGGGTCCTTAGCACCAGCTGCCCAGAGCCCCCAGCCCCTACCCTAGTCTGA<br>TGACCCAGGCCTTTCCCCCTGCCCAGGCTAGCCTTGTGCTCAGCTGCCAGCACAGCCCCCACCAC<br>ACACTCCCAACAGGTGTCTCCACAACTGCCAGGAGACAGCTCAGCTTAGCTGCTCTTCCCCCAA<br>CCCCCAGGCCCAGCAGAATCACATCTAGGAGAGTGGGCCACATGCCTCTTGGAAGGCAGGTGGCA<br>CAAGAGGTTCATCCCACCCTTCCAGCATTACCCAGCCCCACAGGACCCCACATCCTGCTCCCAGCTC<br>CAGCCTGAAAGGAGCTAGTCCTCTCCAGCC (SEQ ID NO: 8) | [C/T] |
| CUBN | rs11254363 | GTGCTCGAGGCTCAAGGTCCCAAAAGTAAATGTTACCAGGAGGTCAGGACTAGTTACAACAATCC<br>AGACACAATCTCTTCCTGGGGGATAGTTTCCAGGATACCCCGGAGACTTAATAGAACCGTAAGGA<br>CCAGTCAGGATACCTCCACACTCTAAAATAAGAGGGAAAAATAATGTTACATTTGTATAGATGCT<br>ATAAATTTATGGAGAATGATCAGAGCCCTTGGCGTAAGAAGCCAAACTTTGTTTAAATAACTATGA<br>GCAGTTTTAGACACCCTCATAAATTAAAAAAGATTTACATTTTCCAGTTTTATAAAGTTACAAGT<br>CTAGAAGTATCAATTGATAAACAAATGAATCACCCATGTGTCAAGCTCTGTGCTTGTGAGCCATC<br>ACATGCTGACACTATTTAAACAGGGCTGAACCATCTGAGCGATGAATACCAGGATTGTAGAGTCA<br>TCTTTTTCACTTTGATGATATTAATTTCTGTATGTGAAATTGTAA[A/G]GAATTCCAGAACTTC<br>TGCCAACCTCTGTGTGTTTCAGCAAACCAGATCACTTTGCATATTAAAATGGTTAAGTGTGACAT<br>AATTTTCATTTGAGAAGGTTTCTTAATACTATCATATAGTTAAAACATTCATTTAATAAATGAAA<br>AAATTCAAATGTCTGTAGTGATCGAGCCACTGTTCCAAGAATGGAGCAAGTGAGGGACTGAGCCA<br>GGCTTTCTGATGCTGACCCCACTACCATCCTCATTATACCACATCGGCCCCTAACGTTGCTGAC<br>TAGTGACTGGAAGAACCTGCTCTTCATTAATACCCACATTTATTTAACAAAGAATCTGTAGTGGC<br>TTAGATTTCTATGAGAAATGCTACTGTAAATCAAATGACAGAAACACTAAATAATAAAAATCCAG<br>ACTGTAGTAATACAGACATTTAGAAATAAGTGAGATAGGTAACATTTTAGATGTGTAAGATATGAA<br>ATTTACATAGCTATACAGGTTGTTCAAATA (SEQ ID NO: 9) | [A/G] |
| CUBN | rs1801222 | tgatctcgaactcctgacctcaggtgatccaccgcctcagccccgcaaagcgctgcgattacag<br>gcatgagccaccgtgcccggccGAAATGGGACCATTTTTATTATCCCGTCATGACTCTCTCTGAG<br>ATAAGACCTTCTCTTGGCCTTGTAAGTTTTATTTTAACAGTGACAAAACACAGGAATATAAAAGG<br>ACCAGTCTTGTTGGCAACATGTGGTTTCAAGGAGTCTGACTTTTCCCGGCCTGGGTCTCTGGAAC<br>TGCTGCAGACTCTAAGAGCCCACTCCCCAGAACGACCCTCCATGCCCTGCGTCCTGATGACTTTG<br>ACTCCTGACCCTCAAGGTTGTCCAGTCTTGGCTGGCTTGGCTCTTCATGAGAACTTCAATTCTTT<br>ATTTTTAGTTGTATTTTTTCTACCCATGTGATGGAAAATAATTCCCGTCCAATGATGGGGATGGA<br>AGGGTTGAGGAGGTGGGTAGGAGGAAGAACTTTCCAAAGAAAAACAAACGGAATTGATTTTCCAA<br>GGTCTGTGCCTACATGGGTGTTTTTCCCTCTAAAAACATAGCAGGCTGAGTTGATTGACTTTAAT<br>TATATTGACTTACAGTTCTTGATTGTTGTTACTCTTTCCCTGGCATCTTTGGGAGAAATTATAGC<br>TTGCTTTTACTCTGAAATAAAGATGTTTCCCTTTTTGCATGGTCTGGTCTAAATGCTTAATCATA<br>TGGGAAGAAAAAGAGAAGCCAGTGGATTGGCCTTATGGAAATGAACGTTAGAGGGATAAACAGTTA<br>GGGGCTTGATGAAATGTTCAAAGGCTTTTCTTGCTGATTTTCATGATTGTCTTTATTCACGCTGT<br>TGTCATCCTGCCAGCCCAAGTACAGCTGCGTCTGTGATGCTGGGTGGATGTYTTCACCCAACAGC<br>CCTGCCTGCACGCTGGACAGAGACGAGTGCAGCTTCCAGCCCGGGCCTTGCTCCACACTTGTGCA | [C/T] |

TABLE 2-continued

SNP Context Sequence

| Target Gene | rsID | Context sequence | SNP |
|---|---|---|---|
| | | GTGTTTCAACACTCAAGGCTCTTTCTACTGTGGGGCCTGTCCAACAGGTACATTCTCAGGGCCAC<br>AAGCCAGGCTCTGCATGCCAGGTTGGCGAGGTGCCAGAACCAATTTTCTTTCACTATTGATGAGT<br>AAGAAGACAATTCTTAGGAGGTGTTCAAATCCAGTTTTGTGTCCTGGTTCTGCTCGACGATCTCA<br>CTGCTATCACAATTCCACGTCAAAAGGGGGAGGCTTGTCCAAAACTGTGCTAGA (SEQ ID NO: 10) | |
| FIGN | rs2119289 | TGCATGTTAATGAAGAGCTTTCTTGCTGTGGATTTCCCTCAAATTTCATTTTAAAAAGCTAGAAT<br>TGTGCAGTTTAAACTTATATAAAGAAAAGAGAGTGTCCAGAGTAACTTAATCATCATGATTTTTG<br>TATTTGACTTATTTCAGAGTCAGGGAATCCTAAAGGAGAATCTCAGACACCAGTGGAAAATTAAA<br>CAGCAAAAGCTCCAATTTCATATCACTGAATCACATAGCTTGAAAGGAATTTGTA[C/G]GCCAT<br>TAGTTTAGCCCCTTCATCTTACAGTTAAGGGGGCTGAAACCCAGAGTTCTTACAGATCAGGAATG<br>GCAGAGCCAGGCTTAGGCCTCCTCTACCAATCTAGGAAACGTTCCATTATACCACTTTGACTGCC<br>TTACACCTTTTCAGAAAATTAAAAATTCACATACTGGAATATAATTATAATGTTAAAGATACTCC<br>TTCAGAGGCAAATGAGTTAGAAATCCGATGCGGAAGAAGAAAATGAGATT (SEQ ID NO: 11) | [C/G] |
| SARDH | rs573904 | CTCAGTCCTGGTGGCTCTGTCCAGGAAAGGGGCTTCTGCCCTCTGGACAGCTGCCTGGAGTTTCC<br>AGCTCTGGCCCCAGCTTCACTCTCCAGGCCACACAAGCAGCATCTGCTCCCTCCTCCCACCACAG<br>CTCTTCAGCGACTGGGAGGGCAAGCAGTGCCCCCAGCTCCGCCCACCTGCAAACTGGCCATGCAC<br>CCTTCCCCAGGGTCTCTTCCCCAGGCTGGTTGTTGTGAACCAAGAACTGTCCCAGCTAGCAATGG<br>GCTGTGGCCCCTCGCTATGTCCTATCCTTCCCTGCCCCTACCTGGCCCCCGGTCCCTACCTGCCG<br>TGTGCCAGGTGGTCCCGGAGGTCAGCCGCTCCCGCTCCAGCAGCACCGCCCCACTCATGCCCAGC<br>TTGGCCAGGTGGTACAGGGTCTGGCAGCCCAAGCTGCCTCCACCAATGACCACCACGTTGGCCGT<br>GCTGGGCAGGGGCCGGCTTGGGCTTGGGCCACCACCGAGGTGCC[C/T]TGTCCCTCCTTCAGG<br>GTCCGCTGATATGGCACACTCTTCTCGGCTGTGGGGCCAGCTGCGCTGGACAGGTTGCATGGCCC<br>CATGCCCCGGGTAGGGCTCTGGCGAGGGTGGGCAGCAGCCACACGTAGGGCTCGGCTCAGTGAGG<br>CCATGGGGGCTCCAGGCCTCAGCGAAACAGGGAGCTGGGGAGAGAATCAGAGCTGGGTGGGGTGC<br>AGAGGGGACACGCTGGGGGCTGTGCTGAGTACCCAGGGAAATAAGGGCCCTATGGTGTTACCTCC<br>CAGGGCCTTCCTCTTGCCACTTTCCCATGGCATTCATTCATTCACTCATTCATTCATTCATTCAC<br>TCATTCATTCATTCACTCATTCATTCATTCACTCATTCATTCACTCATTCATTCATTCATTCACT<br>CATTCATTCACTCATTCATTCATTCATTCACTCATTCATTCATTCATTCATTCTGTGTGTATGTA<br>TTAAGGGCTGGTATGCAGCAGGCTCTGTC (SEQ ID NO: 12) | [C/T] |
| MTHFR | rs1801131 | TCCGGCTCCCTCTAGCCAATCCCTTGTCTCAATTCTCTGTCCCCATCCTCACCCAGGCGTCCCCT<br>ACCCTGGGCTCTCAGCGCCCACCCCAAGCGCCGAGAGGAAGATGTACGTCCCATCTTCTGGGCCT<br>CCAGACCAAAGAGTTACATCTACCGTACCCAGGAGTGGGACGAGTTCCCTAACGGCCGCTGGTGA<br>GGGCCTGCAGACCTTCCTTGCAAATACATCTTTGTTCTTGGGAGCGGGAGGGCAGAAGAAGTTTG<br>CATGCTTGTGGTTGACCTGGGAGGAGTCAGGGGCAGAATTTACAGGAATGGCCTCCTGGGCATGT<br>GGTGGCACTGCCCTCTGTCAGGAGTGTGCCCTGACCTCTGGGCACCCCTCTGCCAGGGGCAATTC<br>CTCTTCCCCTGCCTTTGGGGAGCTGAAGGACTACTACCTCTTCTACCTGAAGAGCAAGTCCCCCA<br>AGGAGGAGCTGCTGAAGATGTGGGGGGAGGAGCTGACCAGTGAAG[A/C]AAGTGTCTTTGAAGT<br>CTTCGTTCTTTACCTCTCGGGAGAACCAAACCGGAATGGTCACAAAGTGAGTGATGCTGGAGTGG<br>GGACCCTGGTTCATCCCCTGCCCCTGGCCTGACCCCAGCTGCAGGCCAGGCTGCGGGGCTGTGAC<br>TTCCCCATCCTGTGCCCTCCCCTCCATGCTGTGGACATGGCAAAGGGAGAAGGGTAAGTTGGGAG<br>ACCTCCACCTGGAAGGGCTTAGGGAGGCAAAGACAGGCTGGGTCTTTGTTGGGGGCCGTGAGAGG<br>GACTCAGGGTGCCAAACCTGATGGTCGCCCCAGCCAGCTCACCGTCTCTCCCAGGTGACTTGCCT<br>GCCCTGGAACGATGAGCCCCTGGCGGCTGAGACCAGCCTGCTGAAGGAGGAGCTGCTGCGGGTGA<br>ACCGCCAGGGCATCCTCACCATCAACTCACAGCCCAACATCAACGGGAAGCCGTCCTCCGACCCC<br>ATCGTGGGCTGGGGCCCCAGCGGGGGCTAT (SEQ ID NO: 13) | [A/C] |
| MTHFR | rs1801133 | TTCAGTGTTACATTAAAAACAATGTTTAATCCGGTGCCTAGAGAAAAGTCAAGCTTACTACCCCA<br>GATGCTGCCCAGCCAGTGCTAACTGTAGCATTTTCTCTTTTCTATGGCCACCAAGTGCAGGCCTG<br>ATTTGCTTGGCTGCTCAAGGCAGGACAGTGTGGGAGTTTGGAGCAATCCACCCCCACTCTTGGAA<br>CTGGGCTCTGAGCCACCTCCCCTGAGAGTCATCTCTGGGGTCAGAAGCATATCAGTCATGAGCCC<br>AGCCACTCACTGTTTTAGTTCAGGCTGTGCTGTGCTGTTGGAAGGTGCAAGATCAGAGCCCCCAA<br>AGCAGAGGACTCTCTCTGCCCAGTCCCTGTGGTCTCTTCATCCCTCGCCTTGAACAGGTGGAGGC<br>CAGCCTCTCCTGACTGTCATCCCTATTGGCAGGTTACCCCAAAGGCCACCCCGAAGCAGGGAGCT<br>TTGAGGCTGACCTGAAGCACTTGAAGGAGAAGGTGTCTGCGGGAG[C/T]CGATTTCATCATCAC<br>GCAGCTTTTCTTTGAGGCTGACACATTCTTCCGCTTTGTGAAGGCATGCACCGACATGGGCATCA<br>CTTGCCCCATCGTCCCCGGGATCTTTCCCATCCAGGTGAGGGGCCCAGGAGAGCCCATAAGCTCC<br>CTCCACCCCACTCTCACCGCACCGTCCTCGCACAGGCTGGGGCTCTGGGTGGAGTGCTGAGTTC<br>GCTGAGTTCTTCCCAGATCTCCTCTCAGGTCCAGAACTTGCACAGCGTTGCTTGGCCACCCCATT<br>TTGGTTACCTCTAATTTTCCCCCCAAAACCCAGCAACAGTGTCTGTTGAGGGGTTTGTTGTACTT<br>TGGCCAACAAGCATCACCAAAAGGGATTCTAATTCTCATTACAAATCCTGCTTAAATCAGTGTTT<br>CCCAAAGGTGGCTGTCATCAGAACCACTTGATAAGCTTTTTCAAAAGTGGATCTCCAGGTCCCA<br>CCCCTGGAGGTTCTCACTCAGTAAATCTGA (SEQ ID NO: 14) | [C/T] |
| MTR | rs1805087 | GGCCCAGAATGCCCATGTGTCTAGCCTTAATTGTTCAGTCTTCAGTCCCTGCAGAGGTCAAACAT<br>AAGCATGAGCGAAGGTCCCCCACCATAAATCAGACTGTTAGCATAAACGATGTGACGTGGCCCAG<br>GGTGCCAGGTATACAGTGACTCTCTTATCAGGCCAGGCTGTCCCAAGGGTTTAGAGTTTGTCTCA<br>AGAAACCAGTCAAAGGCCAGTCCCTTCTTTGGCTTGTGCAGGGTTTGAACATCCCAAGCCCACTG<br>AGTTTACCTTTTCCTGCACGCCAGGCAGGAATTAGCACAGTTGGTGAAGGGAGAAGAAATGAAGT<br>TAAGGAAGCCTTCCTGAAGGAGGTGTTATCAGCATTGACCATTACTACACCAGTTTTATCATCTT<br>TTGCTCATCTATGGCTATCTTGCATTTTCAGTGTTCCCAGCTGTTAGATGAAAATCTAAAGGATG<br>AATACTTTGAGGAAATCATGGAAGAATATGAAGATATTAGACAGG[A/G]CCATTATGAGTCTCT | [A/G] |

TABLE 2-continued

SNP Context Sequence

| Target Gene | rsID | Context sequence | SNP |
|---|---|---|---|
| | | CAAGGTAAGTGGTAGAAACAGATTTTTGCTTGTTTTTAATGTGACTGTTTTTTATGATCCTAGTT<br>TTTAATGTGACTTTTTAAAATGGTTTTGAGGAGTGTAAAAGGCTTTGGATCATTTTAGAGAATTT<br>CTGTCTTCTAGTTCAAATCAGAGGTCTTCAGTGTCTTAAGTTCCCAAATAATTTTTGGTTGTATT<br>GAAATGAATTTTATTTATTCAGCCAAACATTTACTGGGTACCCAGTAGGTGTTAGGGGCTGTGCT<br>AGATATCAGAACTATGGTAATGAATAAAACATGAGTTCATACTCAGCAGGGAAACAGGTGCTGAA<br>ACAGTGTACTGAAATGACTCCCACAGACCCCCATTCTTCAGGAGCTAATGGAAGAAAATGGAGAC<br>ATGAGGCAGGACCAGTATAAGCCTTTTGCCTGACTGCCCAACACTGACTGTGCAGAATGATGTTT<br>TAAGAACTGTCCGTCTCTTGATCAGCTTCA (SEQ ID NO: 15) | |
| SLC19A1 | rs1051266 | GCCCAGCAGTGCCATGAGTCTAGTGTGGCCCCAAACCCTAAATTTTGTTAGTTTAGTTAATAAAG<br>TAAGTCAATTAGTTAATTAACTTGGTTTTGATTGGCACTTAAATCACTCCATGTGGCTGGAGACT<br>TCCCTCAGCCTCGGAGACCCTGGAGGTGGTGACAGCCTGGCCTGGGGGACTCCGGAGCAGCTCAG<br>GTGTGGGTGGCTCCCAGTTTGGTGCTACGGGGTGAGGATGGGTCTGGGGTCTGCATTCGTCTCCA<br>GGGTGGCGTTTGGTCCTGAGTGGCGAGGAGGCCGGCACTGGGCCTCGTTTTGCGGGGTAGGGAGG<br>CCTGCAGACCATCTTCCAAGGTGCCCTGACTCCACCCCTCCTTCCAGGCACAGCGTCACCTTCGT<br>CCCCTCCGGAGCTGCACGTGGCCTGAGCAGGATGGTGCCCTCCAGCCCAGCGGTGGAGAAGCAGG<br>TGCCCGTGGAACCTGGGCCTGACCCCGAGCTCCGGTCCTGGCGGC[A/G]CCTCGTGTGCTACCT<br>TTGCTTCTACGGCTTCATGGCGCAGATACGGCCAGGGGAGAGCTTCATCACCCCCTACCTCCTGG<br>GGCCCGACAAGAACTTCACGCGGGAGCAGGCATGTGGGTGCCGGGGTGCCGGGCGGCCGCCTGTG<br>GGTGGGTGGGCGGGGAGCAGCGTCTGGAATAGGCACGTGGGCGCCGGGATGCGGGGGCGGCCGCC<br>AGTGGGTGGGCAGGGAGCAGCTTCTGGAATAGGCACGTGGGCGCTGGGTGCCAGGGCGGCTGCCT<br>GTGGGTGGGCGGGGAGCAGCTTCTGGAATAGGCACGTGGGTGCCGGGGTGCCGGGCGGCCGCCTG<br>TGGGTGGGCGGGGAGCAGCTTCTGGAATAGGCATGTGGGCACCGGGGTGCTGGGCGGCCGCCTGT<br>GGGTGGGCGGGGAGCAGCTTCTGGAATAGGCACGTGGGTGCTGGGTGCCAGGGCGGCCGCCTATG<br>GGTGGGCGGGGAGCAGCTTCAGGGGCCAGG (SEQ ID NO: 16) | [A/G] |

The TaqMan® OpenArray® genotyping system (Life Technologies Corp., Calsbad, Calif.) can be employed as a high-throughput platform for genotyping subject-derived DNA samples at each of the 16 SNPs identified in Table 1.

For each SNP, two allele-specific probes were provided. Each of the allele-specific probes is conjugated to a fluorescent dye, a quencher and a minor groove binding (MGB) domain. The fluorescent reporter dyes are chosen so that the probe specific for the risk allele is distinguishable from the probe specific for the non-risk allele at the SNP in question. For example, the fluorophores VIC and 6-FAM were employed and were covalently attached to the 5' end of the respective allele-specific probe. Near the 3' end of the allele-specific probe, a non-fluorescent quencher was attached. The MGB increases the melting temperature (Tm) of the probes providing great separation between matched and mismatched probes and thereby increasing genotyping accuracy. Also provided are forward and reverse primers that flank the SNP of interest.

Pre-designed primers and allele-specific probes are commercially available for the TaqMan® genotyping system. For example, TaqMan genotyping reagents for rs7903146 in TCF7L2 are available from Life Technologies under the product code C_29347861_10.

Further details of the TaqMan® genotyping system and OpenArray® format are available from the Life Technologies, Applied Biosystems, webpage, e.g., the TaqMan® OpenArray® Genotyping Getting Started Guide, © 2010 Life Technologies Corporation.

The invention claimed is:

1. A genotyping tool for use in a method of assessing Gestational Diabetes Mellitus (GDM) susceptibility in a female human subject, said tool comprising an array having a plurality of oligonucleotide probe pairs, each of said probe pairs comprising a first probe specific for a first allele of a single nucleotide polymorphism (SNP) and a second probe specific for a second allele of the SNP, wherein said plurality of oligonucleotide probe pairs comprises probe pairs that interrogate each of the following SNPs:

TCF7L2—rs7903146;
IGF2BP2—rs4402960;
CDKN2A/B—rs10811661;
SLC16A11—rs13342232;
FTO—rs8050136;
SLC30A8—rs13266634;
CDC123/CAMK1D—rs12779790;
KCNQ1—rs2237892;
CUBN—rs11254363;
CUBN—rs1801222;
FIGN—rs2119289;
FIGN—rs982393;
MTHFR—rs1801131;
MTHFR—rs1801133;
MTR—rs1805087; and
SLC19A1—rs1051266,
wherein the oligonucleotide probes of the array that interrogate each of the SNPs make up at least 50% of the total number of nucleic acid probes in the array.

2. The genotyping tool according to claim 1, wherein the tool is a nanoliter scale SNP genotyping platform.

3. The genotyping tool of claim 2, wherein the nanoliter scale SNP genotyping platform comprises between 1000 and 10000 array positions.

4. The genotyping tool according to claim 1, wherein the tool is an integrated fluidic circuits (IFC) genotyping platform.

5. The genotyping tool of claim 1, wherein the total number of different SNPs for which allele-specific probes are provided does not exceed twenty.

6. The genotyping tool of claim 1, wherein the allele-specific oligonucleotide probes are each covalently attached to a fluorophore.

7. The genotyping tool of claim 1, wherein the nucleotide sequence of the allele-specific probes is:
(i) a contiguous nucleotide sequence of 13-18 nucleotides, of the sequence context set forth for each SNP as follows: rs7903146 (SEQ ID NO: 1); rs4402960 (SEQ ID NO: 2); rs10811661 (SEQ ID NO: 3); rs13342232 (SEQ ID NO: 4); rs8050136 (SEQ ID NO: 5); rs13266634 (SEQ ID NO: 6); rs12779790 (SEQ ID NO: 7); rs2237892 (SEQ ID NO: 8); rs11254363 (SEQ ID NO: 9); rs1801222 (SEQ ID NO: 10); rs2119289 (SEQ ID NO: 11); rs1801131 (SEQ ID NO: 13); rs1801133 (SEQ ID NO: 14); rs1805087 (SEQ ID NO: 15); and rs1051266 (SEQ ID NO: 16), wherein the probe sequence spans the polymorphic position; or
(ii) the complement of (i).

8. The genotyping tool of claim 1, wherein the tool further comprises a primer pair for each of said SNPs, said primer pair for each SNP comprising an oligonucleotide primer that hybridizes to a target sequence upstream of the SNP and an oligonucleotide primer that hybridizes to a target sequence downstream of the SNP.

9. The genotyping tool of claim 1, wherein the tool further comprises one or more reagents for amplification of DNA comprising said SNPs and/or for detection of said allele-specific probes.

* * * * *

SEQUENCE LISTING

```
<160> NUMBER OF SEQ ID NOS: 16

<210> SEQ ID NO 1
<211> LENGTH: 401
<212> TYPE: DNA
<213> ORGANISM: Artificial Sequence
<220> FEATURE:
<223> OTHER INFORMATION: TCF7L2 rs7903146
<220> FEATURE:
<221> NAME/KEY: misc_feature
<222> LOCATION: (201)..(201)
<223> OTHER INFORMATION: n = c or t

<400> SEQUENCE: 1
gcacatgtga aagaaaaagg gagaaagcag gattgagcag ggggagccgt cagatggtaa      60
tgcagatgtg atgagatctc tgccggacca aagagaagat tccttttttaa atggtgacaa    120 attcatgggc tttctctgcc tcaaaaccta gcacagctgt tatttactga acaattagag    180
agctaagcac tttttagata ntatataatt taattgccgt atgaggcacc cttagttttc    240
```

```
agacgagaaa ccacagttac agggaaggca agtaacttag tcaatgtcag ataactagga    300
aaaggttaga ggggccctgg acacaggcct gtgtgactga gaagcttggg cacttcactg    360
ctacatttca tctcttcgct ataaacattt tagcttttg t                        401
```

<210> SEQ ID NO 2
<211> LENGTH: 550
<212> TYPE: DNA
<213> ORGANISM: Artificial Sequence
<220> FEATURE:
<223> OTHER INFORMATION: IGF2BP2 rs4402960
<220> FEATURE:
<221> NAME/KEY: misc_feature
<222> LOCATION: (270)..(270)
<223> OTHER INFORMATION: n = g or a

<400> SEQUENCE: 2

```
gctggagttg gtttctggcc tcctccaggc tcccctgcat caagcgcagc tgagcagttc     60
cctgtaatgg ggagagggtc tgtcccttta tctggagcct ccagttttga aaatcagccc    120
tggatctcca actgctgccc agtctggctg ttcagcaggc cccatgcccc ctttccccca    180
gtcttgaggc ctgggactag ggctgtcagg cacgtctgcc acgtctgccc ctctctcccc    240
tgcggccagc cctctacagc cacaagcccn aggtggccca gtacacccac acgggcctgc    300
tcccgcagac tatgctcatc accgacacca ccaacctgag cgccctggcc agcctcacgc    360
ccaccaagca ggtaaggtcc aggcctgctg cccctccctt ggcctgtgac agagcccctc    420 accccacat cccccgggct caggaggctg ctctgctccc ccaggtcttc acctcagaca    480
ctgaggcctc cagtgagtcc gggcttcaca cgccggcatc tcaggccacc accctccacg    540
tccccagcca                                                          550
```

<210> SEQ ID NO 3
<211> LENGTH: 401
<212> TYPE: DNA
<213> ORGANISM: Artificial Sequence
<220> FEATURE:
<223> OTHER INFORMATION: CDKN2A/B rs10811661
<220> FEATURE:
<221> NAME/KEY: misc_feature
<222> LOCATION: (201)..(201)
<223> OTHER INFORMATION: n = c or t

<400> SEQUENCE: 3

```
atattgacaa agtttcagtt aagcagatga aattctaaga gttaagctgg gattttccaa     60
aataatcctg ttaacagact tgaaagcact tatcagttct gtctaatgaa gacattagaa    120
caccataacc tttccggccc attttctttg tcaataagcg ttcttgccct gtcagcagct    180
cacctccagc tttagttttc ncatgacagt aagtctatta ccctcctgat ctgtcttctg    240
gctcctccta cccaggatgg ggaaggtttt tgactttact gatattctca gaacaaattt    300
tgggaagtaa atataaggtt ttccagtcgg gtgcagtggc tcacgcctat gatcccagcg    360
ctttgggaaa ccaaggtggg tggatcacct gaggtcagga g                       401
```

<210> SEQ ID NO 4
<211> LENGTH: 501
<212> TYPE: DNA
<213> ORGANISM: Artificial Sequence
<220> FEATURE:
<223> OTHER INFORMATION: SLC16A11 rs13342232
<220> FEATURE:
<221> NAME/KEY: misc_feature
<222> LOCATION: (251)..(251)
<223> OTHER INFORMATION: n = a or g -continued

<400> SEQUENCE: 4

```
ctaaagcgtg gggagccaag tgcacgtaag gaacgaagta cccgccccca accagggctg    60
tgcctagagc aaagattgag aaggcccggc gtgtgaacag actcaggccg agggcagcta   120
ggggactacg cggtggggct gggggtctc caggaaggac caggggtagc agcagggcgc    180
cacaggggt gaggtggagg gtgatcgcgc cgaggaggag cagagcgccc cgccagccga    240
aagtatcgag nagaagctgc aaggcgggcg ccaggacag cgaggaggcc ccgttgccgg    300
tgagcgccag ccccaccgcc aagactcgac ggcgggagaa gtaacgcgag agggtgccta   360
gggcggggc gaacaccagg gcccaaccaa agcctgcgaa tgaataggag gggatggggg    420
ccggcactgg ggacgcccgc cccagcattc ccagcccggc tctccgcacc aggcccccgc   480
ctcgttcgct accccagatc c                                             501
```

<210> SEQ ID NO 5
<211> LENGTH: 1001
<212> TYPE: DNA
<213> ORGANISM: Artificial Sequence
<220> FEATURE:
<223> OTHER INFORMATION: FTO rs8050136
<220> FEATURE:
<221> NAME/KEY: misc_feature
<222> LOCATION: (501)..(501)
<223> OTHER INFORMATION: n = a or c

<400> SEQUENCE: 5

```
ctggcacatc agggttcaga tttctgctgt gctacttctt ggctgtgttt tggcacgtga    60
acttctctac acctcagttt ctttgtttat gtaatgggga ttcatatgac aattaaagag   120
agagcttgtc taaagtgtct tatgtagtag tatccccagt ttgacccttt tgagaatctg   180
atgacagtta tggaaccctc tccccagaca agtgcccgta tacccagaac tttgtattta   240
atttcatggg gttcatgaag cctctgaaac tcagcttaag agtccatacc aaccaaggtc   300
cttataggaa gagcttgtgt ttttgttttg ttttggcttt ctgcagtctc ttaataatgt   360
ttattgaatg agagaattta actaatttcc ggtttccata atcactttaa actcggtatt   420
tgatttcctt ttccctggga cctgtgacag tgccagcttc atagcctagt ctaggcatgc   480
cagttgccca ctgtggcaat naatatctga gcctgtggtt tttgccttag gtaaactgta   540
gagatggact catggaatgc ttggaaaatt tttcagttta tgataatgtg taaatgtcga   600
gagccaatta ttgaggaatg gcacctcaaa gtatttgggt actctagatc agacatgacc   660
atcttggtgt gtgaaatttt gctaatgcat cttttcctaat agaatataca atctcagggc   720
tagaaagtct tagagatcat ttaatttaat tcctccagat tgattaagtg gtttgtccaa   780
ggtcattcaa ctggtatagt ggcagagctc aggctgtaca aatcaggtga gtattcttca   840
gctcctcaga agccagtaac ttccactcac ttgtgtgtgt ctgaaattca ttaaaccttc   900
gacacaaagt gcagccattt taatgctgaa tgatattcat cactgtctga aatgggctta   960
tttatgtacg aatgtttatt cctatctctt cctccattct c                      1001
```

<210> SEQ ID NO 6
<211> LENGTH: 1001
<212> TYPE: DNA
<213> ORGANISM: Artificial Sequence
<220> FEATURE:
<223> OTHER INFORMATION: SLC30A8 rs13266634
<220> FEATURE:
<221> NAME/KEY: misc_feature
<222> LOCATION: (501)..(501)

<223> OTHER INFORMATION: n = c or t

<400> SEQUENCE: 6

```
ctgctgatag catttgggac aggaaaaaaa tggcagtgag ggttgctgct ctaagaaagg      60
tctgtgggga gctctaaacg cttcctggtt cctgtcacta tccttgatat aaattctgat    120
tacatacaaa gcctgcaacc cagagatccc tgggagctgg tgagcagggc tgtataagaa    180
ataatagttc tgtcttggct ttttccaggg cttgtctccc cttccatagt aagctcctag    240
gaatgccaga ctccagagat aacagtggac agaaagagtt cccatagcga cagggcactt    300
tgctgcacta gagtttcccc tgccttgtct gtgtgaatgt agctgattat cagagcaaac    360
gtggcttcct ctgagtgccc tgcctctgcc ccaccccagc aggtcaaaga caaagtactt    420
gaagttggag tcagagcagt cgcccatgcg tgtgcaatca gtgctaatct ccctgtgctt    480
ctttatcaac agcagccagc nggacagcc aagtggttcg gagagaaatt gctaaagccc     540
ttagcaaaag ctttacgatg cactcactca ccattcagat ggaatctcca gttgaccagg    600
accccgactg cctttctgt gaagacccct gtgactagct cagtcacacc gtcagtttcc     660
caaatttgac aggccacctt caaacatgct gctatgcagt ttctgcatca tagaaaataa    720
ggaaccaaag aagaaaattc atgtcatggt gcaatgcaca ttttatctat ttatttagtt    780
ccattcacca tgaaggaaga ggcactgaga tccatcaatc aattggatta tatactgatc    840
agtagctgtg ttcaattgca ggaatgtgta tatagattat tcctgagtgg agccgaagta    900
acagctgttt gtaactatcg gcaataccaa attcatctcc cttccaataa tgcatcttga    960
gaacacatag gtaaatttga actcaggaaa gtcttactag a                      1001
```

<210> SEQ ID NO 7
<211> LENGTH: 1001
<212> TYPE: DNA
<213> ORGANISM: Artificial Sequence
<220> FEATURE:
<223> OTHER INFORMATION: CDC123/CAMK1D rs12779790
<220> FEATURE:
<221> NAME/KEY: misc_feature
<222> LOCATION: (501)..(501)
<223> OTHER INFORMATION: n = a or g

<400> SEQUENCE: 7

```
agatttggg ctgaggcgat ggggttttct agatatataa tcatgtcatc tgcaaacagg      60
gacaacttga cttctctttt tcctaattga atacccttta tttccttctc ctgcctgatt    120
gccctggcca gaacttccaa cactacgttg actaggggtg gtgagatact tcttttttt    180
cttttttttt gagatggagt ctcgctctgt cgcccaggct ggagtgcagt ggcgtgatct    240
tggctcactg caagctccac ctccgggtt cacaacattc tcctgcctga gccttccgag     300
taggtgggac tgcaggcacc cgccaccacg cgcagctaat ttttttgtat tttagtagaga   360
gatgggttt cactgtgtta gccaggatgg tctcgatctc ctgacctcgt gatccgcctg     420
cctcggcctc ccaaagtctc ccaaagtgct gggattacag gtgtgagcca ccgcacccgg    480
acaatgttgg gaattttttc ntatttcttg gccatttata tatcttcttt tgagaattat    540
ctattcatgt ccttagccca ttttttgatg ggatttttt ttcttgctag tttgtttgtg     600
ttcattgtag attctggata ttagtccttt gtcagatgta tactatttgt atctttttt     660
tttggacaga gtctcactct gctgcccagg ctggagtgca gtggtgtgat cttggctcac    720
tgcaacctcc gcctcctggg ttcaagcaat tctcctacct cagcctcctg agtagctggg    780
actacaggtg cataccacca cacctggcta atttttctgta ttttttttt tttttttgat    840
```

```
agagacgggg tttcaccatg ttagccaggg tgggcttgat ctcctgacct cgtgatccac    900
ccacctcggc ctcccaaagt gctgggatta caggcgtgag ccactgcact cagccctctt    960
ttttattatt aaaatttttt ttggctaggc atggtggctc a                       1001
```

<210> SEQ ID NO 8
<211> LENGTH: 1001
<212> TYPE: DNA
<213> ORGANISM: Artificial Sequence
<220> FEATURE:
<223> OTHER INFORMATION: KCNQ1 rs2237892
<220> FEATURE:
<221> NAME/KEY: misc_feature
<222> LOCATION: (501)..(501)
<223> OTHER INFORMATION: n = c or t

<400> SEQUENCE: 8

```
aatatgcatt aacacctaaa acccactatc ctggcaaaaa agtggcagga ttgtctgaaa     60
aacacatggc cagccaccct gcaccctgag ttccacaaca tctaaaccca gtgtctgctg    120
gccctcagag tgggagcgcg tgccccaact tccgagccct aggaaagggt cttgtctgct    180
cttcccctca gtgtcaggtg acccaagagt gtggggtca  ggaatggcgt ccttgtgccc    240
ttgtcaccca ctcctgtggg tacacagctt ccctttctgc aaagtcacac cccaagccct    300
ggcttgagca tgtacacagg ctgcagcccg tgttcctgga gccaccgtcc caggtgtggc    360
taaggccccc acagagtgtg catcctaagg tggttcagag gtcctcagaa agtgccaaga    420
ggccttcctc agaggaagag caagggtagg tgcctctggc atgagccaga tgatgggagc    480
tgtcacagga ctttgccacc nggggtgagg ggcctagaaa cccctctcca ccagatgcct    540
tacacccccc atccccacac gcacacagct tggaggctgg aagccccgg  aatgcggccc    600 accctgtctc cagttgttcc ctaccagccc agctgctggt ccctaaccgg gcccacctgt    660
tgggtcctta gcaccagctg cccagagccc ccagccccta ccctagtctg atgacccagg    720
cctttccccc tgcccaggct agccttgtgc tcagctgcca gcacagcccc caccacacac    780
tccccaacag gtgtctccac aactgccagg agacagctca gcttagctgc tcttccccca    840
acccccaggc ccagcagaat cacatctagg agagtgggcc acatgcctct tggaaggcag    900
gtggcacaag aggttcatcc cacccctcca g cattacccag ccccacagga cccacatcct   960
gctcccagct ccagcctgaa aggagctagt cctctccagc c                       1001
```

<210> SEQ ID NO 9
<211> LENGTH: 1001
<212> TYPE: DNA
<213> ORGANISM: Artificial Sequence
<220> FEATURE:
<223> OTHER INFORMATION: CUBN rs11254363
<220> FEATURE:
<221> NAME/KEY: misc_feature
<222> LOCATION: (501)..(501)
<223> OTHER INFORMATION: n = a or g

<400> SEQUENCE: 9

```
gtgctcgagg ctcaaggtcc caaaagtaaa tgttaccagg aggtcaggac tagttacaac     60
aatccagaca caatctcttc ctgggggata gtttccagga taccccggag acttaataga    120
accgtaagga ccagtcagga tacctccaca ctctaaaata gagggaaaa  ataatgttac    180 atttgtatag atgctataat ttatggagaa tgatcagagc ccttggcgta agaagccaaa    240
ctttgtttaa ataactatga gcagttttag acaccctcat aaattaaaaa agatttacat    300
```

```
tttccagttt tataaagtta caagtctaga agtatcaatt gataaacaaa tgaatcaccc      360
atgtgtcaag ctctgtgctt gtgagccatc acatgctgac actatttaaa cagggctgaa      420
ccatctgagc gatgaatacc aggattgtag agtcatcttt ttcactttga tgatattaat      480
ttctgtatgt gaaattgtaa ngaattccag aacttctgcc aacctctgtg tgtttcagca      540
aaccagatca ctttgcatat taaatggtt aagtgtgaca taattttcat ttgagaaggt       600
ttcttaatac tatcatatag ttaaaacatt catttaataa atgaaaaaat tcaaatgtct      660
gtagtgatcg agccactgtt ccaagaatgg agcaagtgag ggactgagcc aggctttctg     720
atgctgaccc cactaccatc ctcattatac cacatcggcc ccctaacgtt gctgactagt    780
gactggaaga acctgctctt cattaatacc cacatttatt taacaaagaa tctgtagtgg    840
cttagatttc tatgagaaat gctactgtaa atcaaatgac agaaacacta ataataaaa       900 atccagactg tagtaataca gacattagaa ataagtgaga taggtaacat tttagatgtg      960
taagatatga aatttacata gctatacagg ttgttcaaat a                         1001

<210> SEQ ID NO 10
<211> LENGTH: 1224
<212> TYPE: DNA
<213> ORGANISM: Artificial Sequence
<220> FEATURE:
<223> OTHER INFORMATION: CUBN rs1801222

<400> SEQUENCE: 10
tgatctcgaa ctcctgacct caggtgatcc acccgcctca gccccgcaaa gcgctgcgat      60
tacaggcatg agccaccgtg cccggccgaa atgggaccat ttttattatc ccgtcatgac     120
tctctctgag ataagacctt ctcttggcct tgtaagtttt attttaacag tgacaaaaca     180
caggaatata aaaggaccag tcttgttggc aacatgtggt ttcaaggagt ctgacttttc     240
ccggcctggg tctctggaac tgctgcagac tctaagagcc cactcccag aacgaccctc      300 catgccctgc gtcctgatga cttgactcc tgaccctcaa ggttgtccag tcttggctgg     360
cttggctctt catgagaact tcaattcttt attttagtt gtattttttc tacccatgtg     420
atggaaaata attcccgtcc aatgatgggg atggaaggg tgaggaggtg ggtaggagga      480
agaactttcc aaagaaaaac aaacggaatt gattttccaa ggtctgtgcc tacatgggtg    540
tttttccctc taaaaacata gcaggctgag ttgattgact taattatat tgacttacag    600 ttcttgattg ttgttactct ttccctggca tctttgggag aaattatagc ttgcttttac    660
tctgaaataa agatgtttcc ctttttgcat ggtctggtct aaatgcttaa tcatatggga    720
agaaaaagag aagccagtgg attggcctta tggaaatgaa cgttagagga taaacagtta    780
ggggcttgat gaaatgttca aaggcttttc ttgctgattt tcatgattgt ctttattcac    840
gctgttgtca tcctgccagc ccaagtacag ctgcgtctgt gatgctgggt ggatgtyttc     900
acccaacagc cctgcctgca cgctggacag agacgagtgc agcttccagc ccgggccttg    960
ctccacactt gtgcagtgtt tcaacactca aggctctttc tactgtgggg cctgtccaac   1020
aggtacattc tcagggccac aagccaggct ctgcatgcca ggttggcgag gtgccagaac   1080
caattttctt tcactattga tgagtaagaa gacaattctt aggaggtgtt caaatccagt   1140
tttgtgtcct ggttctgctc gacgatctca ctgctatcac aattccacgt caaaagggg     1200 aggcttgtcc aaaactgtgc taga                                          1224

<210> SEQ ID NO 11
<211> LENGTH: 501
```

<212> TYPE: DNA
<213> ORGANISM: Artificial Sequence
<220> FEATURE:
<223> OTHER INFORMATION: FIGN rs2119289
<220> FEATURE:
<221> NAME/KEY: misc_feature
<222> LOCATION: (251)..(251)
<223> OTHER INFORMATION: n = c or g

<400> SEQUENCE: 11

```
tgcatgttaa tgaagagctt tcttgctgtg gatttccctc aaatttcatt ttaaaaagct     60
agaattgtgc agtttaaact tatataaaga aaagagagtg tccagagtaa cttaatcatc    120
atgattttg  tatttgactt atttcagagt cagggaatcc taaaggagaa tctcagacac    180
cagtggaaaa ttaaacagca aaagctccaa tttcatatca ctgaatcaca tagcttgaaa    240
ggaatttgta ngccattagt ttagcccctt catcttacag ttaagggggc tgaaacccag    300
agttcttaca gatcaggaat ggcagagcca ggcttaggcc tcctctacca atctaggaaa    360
cgttccatta taccactttg actgccttac acctttcag  aaaattaaaa attcacatac    420
tggaatataa ttataatgtt aaagatactc cttcagaggc aaatgagtta gaaatccgat    480
gcggaagaag aaaatgagat t                                              501
```

<210> SEQ ID NO 12
<211> LENGTH: 1001
<212> TYPE: DNA
<213> ORGANISM: Artificial Sequence
<220> FEATURE:
<223> OTHER INFORMATION: SARDH rs573904
<220> FEATURE:
<221> NAME/KEY: misc_feature
<222> LOCATION: (501)..(501)
<223> OTHER INFORMATION: n = c or t

<400> SEQUENCE: 12

```
ctcagtcctg gtggctctgt ccaggaaagg ggcttctgcc ctctggacag ctgcctggag     60
tttccagctc tggccccagc ttcactctcc aggccacaca agcagcatct gctccctcct    120
cccaccacag ctcttcagcg actgggaggg caagcagtgc cccagctcc  gcccacctgc    180
aaactggcca tgcaccctc  cccagggtct cttccccagg ctggttgttg tgaaccaaga    240
actgtcccag ctagcaatgg gctgtggccc ctcgctatgt cctatccttc cctgcccta    300
cctggccccc ggtccctacc tgccgtgtgc caggtggtcc cggaggtcag ccgctcccgc    360
tccagcagca ccgccccact catgcccagc ttggccaggt ggtacagggt ctggcagccc    420
aagctgcctc caccaatgac caccacgttg gccgtgctgg gcaggggccg gcttgggcct    480
tgggccacca ccgaggtgcc ntgtccctcc ttcagggtcc gctgatatgg cacactcttc    540
tcggctgtgg ggccagctgc gctggacagg ttgcatggcc ccatgccccg ggtagggctc    600
tggcgagggt gggcagcagc cacacgtagg gctcggctca gtgaggccat gggggctcca    660
ggcctcagcg aaacagggag ctggggagag aatcagagct gggtgggtg  cagagggggac   720
acgctggggg ctgtgctgag tacccaggga ataagggcc  ctatggtgtt acctcccagg    780
gccttcctct tgccacttcc ccatggcatt cattcattca ctcattcatt cattcattca    840
ctcattcatt cattcactca ttcattcatt cactcattca ttcactcatt cattcattca    900
ttcactcatt cattcactca ttcattcatt cactcattca ttcactcatt cattcattct    960
gtgtgtatgt attaagggcc tggtatgcag caggctctgt c                       1001
```

<210> SEQ ID NO 13

```
<211> LENGTH: 1001
<212> TYPE: DNA
<213> ORGANISM: Artificial Sequence
<220> FEATURE:
<223> OTHER INFORMATION: MTHFR rs1801131
<220> FEATURE:
<221> NAME/KEY: misc_feature
<222> LOCATION: (501)..(501)
<223> OTHER INFORMATION: n = a or c

<400> SEQUENCE: 13
tccggctccc tctagccaat cccttgtctc aattctctgt ccccatcctc acccaggcgt      60
cccctaccct gggctctcag cgcccacccc aagcgccgag aggaagatgt acgtcccatc     120
ttctgggcct ccagaccaaa gagttacatc taccgtaccc aggagtggga cgagttccct     180
aacggccgct ggtgagggcc tgcagacctt ccttgcaaat acatctttgt tcttgggagc     240
gggagggcag aagaagtttg catgcttgtg gttgacctgg gaggagtcag gggcagaatt     300
tacaggaatg gcctcctggg catgtggtgg cactgccctc tgtcaggagt gtgccctgac     360
ctctgggcac ccctctgcca ggggcaattc ctcttcccct gcctttgggg agctgaagga     420
ctactacctc ttctacctga agagcaagtc ccccaaggag gagctgctga agatgtgggg     480
ggaggagctg accagtgaag naagtgtctt tgaagtcttc gttctttacc tctcgggaga     540
accaaaccgg aatggtcaca aagtgagtga tgctggagtg gggaccctgg ttcatcccct     600 gccctggcc tgaccccagc tgcaggccag gctgcgggc tgtgacttcc ccatcctgtg      660 ccctccctc catgctgtgg acatggcaaa gggagaaggg taagttggga gacctccacc     720
tggaagggct tagggaggca aagacaggct gggtctttgt tggggccgt gagagggact      780 cagggtgcca aacctgatgg tcgccccagc cagctcaccg tctctcccag gtgacttgcc     840
tgccctggaa cgatgagccc ctggcggctg agaccagcct gctgaaggag gagctgctgc     900
gggtgaaccg ccagggcatc ctcaccatca actcacagcc caacatcaac gggaagccgt     960
cctccgaccc catcgtgggc tggggcccca gcgggggcta t                       1001

<210> SEQ ID NO 14
<211> LENGTH: 1001
<212> TYPE: DNA
<213> ORGANISM: Artificial Sequence
<220> FEATURE:
<223> OTHER INFORMATION: MTHFR rs1801133
<220> FEATURE:
<221> NAME/KEY: misc_feature
<222> LOCATION: (501)..(501)
<223> OTHER INFORMATION: n = c or t

<400> SEQUENCE: 14
ttcagtgtta cattaaaaac aatgtttaat ccggtgccta gagaaaagtc aagcttacta      60
ccccagatgc tgcccagcca gtgctaactg tagcattttc tcttttctat ggccaccaag     120
tgcaggcctg atttgcttgg ctgctcaagg caggacagtg tgggagtttg agcaatcca      180 cccccactct tggaactggg ctctgagcca cctcccctga gagtcatctc tggggtcaga     240
agcatatcag tcatgagccc agccactcac tgttttagtt caggctgtgc tgtgctgttg     300
gaaggtgcaa gatcagagcc cccaaagcag aggactctct ctgcccagtc cctgtggtct     360
cttcatccct cgccttgaac aggtggaggc cagcctctcc tgactgtcat ccctattggc     420
aggttacccc aaaggccacc ccgaagcagg gagctttgag gctgacctga agcacttgaa     480
ggagaaggtg tctgcgggag ncgatttcat catcacgcag cttttctttg aggctgacac     540
attcttccgc tttgtgaagg catgcaccga catgggcatc acttgcccca tcgtccccgg     600
```

```
gatctttccc atccaggtga ggggcccagg agagcccata agctccctcc acccactct      660 caccgcaccg tcctcgcaca ggctgggggc tctgggtgga gtgctgagtt cgctgagttc     720
ttcccagatc tcctctcagg tccagaactt gcacagcgtt gcttggccac cccattttgg     780
ttacctctaa ttttccccccc aaacccagc aacagtgtct gttgaggggt ttgttgtact     840
ttggccaaca agcatcacca aaagggattc taattctcat tacaaatcct gcttaaatca     900
gtgtttccca aaggtggctg tcatcagaac cacttgataa gcttttttcaa aaagtggatc    960 tccaggtccc acccctggag gttctcactc agtaaatctg a                         1001
```

<210> SEQ ID NO 15
<211> LENGTH: 1001
<212> TYPE: DNA
<213> ORGANISM: Artificial Sequence
<220> FEATURE:
<223> OTHER INFORMATION: MTR rs1805087
<220> FEATURE:
<221> NAME/KEY: misc_feature
<222> LOCATION: (501)..(501)
<223> OTHER INFORMATION: n = a or g

<400> SEQUENCE: 15

```
ggcccagaat gcccatgtgt ctagccttaa ttgttcagtc ttcagtccct gcagaggtca      60
aacataagca tgagcgaagg tccccccacca taaatcagac tgttagcata aacgatgtga    120
cgtggcccag ggtgccaggt atacagtgac tctcttatca ggcaggctgt cccaagggtt     180
tagagtttgt ctcccagaaa ccagtcaaag gccagtccct tctttggctt gtgcagggtt     240
tgaacatccc aagcccactg agtttacctt ttcctgcacg ccaggcagga attagcacag     300
ttggtgaagg gagaagaaat gaagttaagg aagccttcct gaaggaggtg ttatcagcat     360
tgaccattac tacaccagtt ttatcatctt ttgctcatct atggctatct tgcattttca     420
gtgttcccag ctgttagatg aaaatctaaa ggatgaatac tttgaggaaa tcatggaaga     480
atatgaagat attagacagg nccattatga gtctctcaag gtaagtggta gaaacagatt     540
tttgcttgtt tttaatgtga ctgttttttta tgatcctagt ttttaatgtg acttttttaaa   600 atggttttga ggagtgtaaa aggctttgga tcattttaga gaatttctgt cttctagttc     660
aaatcagagg tcttcagtgt cttaagttcc caaataattt ttggttgtat tgaaatgaat     720
tttatttatt cagccaaaca tttactgggt acccagtagg tgttaggggc tgtgctagat     780
atcagaacta tggtaatgaa taaaacatga gttcatactc agcagggaaa caggtgctga     840
aacagtgtac tgaaatgact cccacagacc cccattcttc aggagctaat ggaagaaaat     900
ggagacatga ggcaggacca gtataagcct tttgcctgac tgcccaacac tgactgtgca    960
gaatgatgtt ttaagaactg tccgtctctt gatcagcttc a                        1001
```

<210> SEQ ID NO 16
<211> LENGTH: 1001
<212> TYPE: DNA
<213> ORGANISM: Artificial Sequence
<220> FEATURE:
<223> OTHER INFORMATION: SLC19A1 rs1051266
<220> FEATURE:
<221> NAME/KEY: misc_feature
<222> LOCATION: (501)..(501)
<223> OTHER INFORMATION: n = a or g

<400> SEQUENCE: 16

```
gcccagcagt gccatgagtc tagtgtggcc ccaaacccta aatttgtta gtttagttaa       60
```

-continued

```
taaagtaagt caattagtta attaacttgg ttttgattgg cacttaaatc actccatgtg    120
gctggagact tccctcagcc tcggagaccc tggaggtggt gacagcctgg cctgggggac    180
tccggagcag ctcaggtgtg ggtggctccc agtttggtgc tacggggtga ggatgggtct    240
ggggtctgca ttcgtctcca gggtggcgtt tggtcctgag tggcgaggag gccggcactg    300
ggcctcgttt tgcggggtag ggaggcctgc agaccatctt ccaaggtgcc ctgactccac    360
ccctccttcc aggcacagcg tcaccttcgt ccctccgga gctgcacgtg gcctgagcag     420
gatggtgccc tccagcccag cggtggagaa gcaggtgccc gtggaacctg ggcctgaccc    480
cgagctccgg tcctggcggc ncctcgtgtg ctacctttgc ttctacggct tcatggcgca    540
gatacggcca ggggagagct tcatcacccc ctacctcctg gggcccgaca agaacttcac    600
gcgggagcag gcatgtgggt gccggggtgc cgggcggccg cctgtgggtg ggtgggcggg    660
gagcagcgtc tggaataggc acgtgggcgc cgggatgcgg gggcggccgc cagtgggtgg    720
gcagggagca gcttctggaa taggcacgtg ggcgctgggt gccagggcgg ctgcctgtgg    780
gtgggcgggg agcagcttct ggaataggca cgtgggtgcc ggggtgccgg gcggccgcct    840
gtgggtgggc ggggagcagc ttctggaata ggcatgtggg caccggggtg ctgggcggcc    900
gcctgtgggt gggcggggag cagcttctgg aataggcacg tgggtgctgg gtgccagggc    960
ggccgcctat gggtgggcgg ggagcagctt caggggccag g                       1001
```